(12) United States Patent
Thompson

(10) Patent No.: US 11,873,505 B2
(45) Date of Patent: *Jan. 16, 2024

(54) COMPOSITIONS AND METHODS FOR REGULATING PRODUCTION OF A PRECURSOR PROTEIN

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 195 days.

This patent is subject to a terminal disclaimer.

(21) Appl. No.: 17/132,385

(22) Filed: Dec. 23, 2020

(65) Prior Publication Data

US 2022/0170043 A1 Jun. 2, 2022

Related U.S. Application Data

(63) Continuation of application No. 17/105,967, filed on Nov. 27, 2020.

(51) Int. Cl.
*A61K 35/763* (2015.01)
*C12N 15/86* (2006.01)
*C07K 14/705* (2006.01)

(52) U.S. Cl.
CPC ............ *C12N 15/86* (2013.01); *C07K 14/705* (2013.01); *C12N 2750/14141* (2013.01)

(58) Field of Classification Search
CPC ..... A61K 35/763; C07K 14/705; C12N 15/86
See application file for complete search history.

(56) References Cited

U.S. PATENT DOCUMENTS

2018/0318365 A1* 11/2018 Yeung ................ A61K 38/2013

FOREIGN PATENT DOCUMENTS

| WO | WO 04/094671 | * | 11/2004 |
| WO | WO 07/051201 | * | 5/2007 |
| WO | WO 09/010769 | * | 1/2009 |

OTHER PUBLICATIONS

GenBank NM_001279752.1, Gorilla TLR3, 2016.*
Matsumoto et al, Establishment of a monoclonal antibody against human Toll-like receptor 3 that blocks double-stranded RNA-mediated signaling, Biochem. & Biophys. Res. Comm. 293: 1364-1369, 2002.*
Wang et al, Toll-Like Receptor 3 Mediates Establishment of an Antiviral State against Hepatitis C Virus in Hepatoma Cells, J. Virol. 83(19): 9824-9834, 2009.*
GenBank KJ411914, cloning vector pAAV-CB-EGFP; 2014.*

* cited by examiner

*Primary Examiner* — Kevin K Hill
(74) *Attorney, Agent, or Firm* — Gowling WLG (Canada) LLP

(57) ABSTRACT

The present disclosure relates to one or more agents, therapies, treatments, and methods of use of the agents and/or therapies and/or treatments for increasing production of a TLR3 precursor protein. Embodiments of the present disclosure can be used as a therapy or a treatment for a subject that has a condition whereby the subject's immune system is, or is likely to become, dysregulated and where the production of the TLR3 precursor protein may result in an increased production of a functional and bioavailable TLR3 protein product, which may be of therapeutic benefit.

3 Claims, No Drawings

Specification includes a Sequence Listing.

SEQUENCE LISTING

<160> NUMBER OF SEQ ID NOS: 2

<210> SEQ ID NO 1
<211> LENGTH: 2715
<212> TYPE: DNA
<213> ORGANISM: Artificial Sequence
<220> FEATURE:
<223> OTHER INFORMATION: Synthetic Sequence

<400> SEQUENCE: 1

| | | | | | |
|---|---|---|---|---|---|
| atgcgccaga | ccctgccgtg | catttatttt | tggggcggcc | tgctgccgtt | tggcatgctg | 60 |
| tgcgcgagca | gcaccaccaa | atgcaccgtg | agccatgaag | tggcggattg | cagccatctg | 120 |
| aaactgaccc | aggtgccgga | tgatctgccg | accaacatta | ccgtgctgaa | cctgacccat | 180 |
| aaccagctgc | gccgcctgcc | ggcggcgaac | tttacccgct | atagccagct | gaccagcctg | 240 |
| gatgtgggct | taacaccat | tagcaaactg | gaaccggaac | tgtgccagaa | actgccgatg | 300 |
| ctgaaagtgc | tgaacctgca | gcataacgaa | ctgagccagc | tgagcgataa | aacctttgcg | 360 |
| ttttgcacca | acctgaccga | actgcatctg | atgagcaaca | gcattcagaa | aattaaaaac | 420 |
| aacccgtttg | tgaaacagaa | aaacctgatt | accctggatc | tgagccataa | cggcctgagc | 480 |
| agcaccaaac | tgggcaccca | ggtgcagctg | aaaacctgc | aggaactgct | gctgagcaac | 540 |
| aacaaaattc | aggcgctgaa | aagcgaagaa | ctggatattt | ttgcgaacag | cagcctgaaa | 600 |
| aaactggaac | tgagcagcaa | ccagattaaa | gaatttagcc | cgggctgctt | tcatgcgatt | 660 |
| ggccgcctgt | ttggcctgtt | tctgaacaac | gtgcagctgg | gcccgagcct | gaccgaaaaa | 720 |
| ctgtgcctgg | aactggcgaa | caccagcatt | cgcaacctga | gcctgagcaa | cagccagctg | 780 |
| agcaccacca | gcaacaccac | ctttctgggc | ctgaaatgga | ccaacctgac | catgctggat | 840 |
| ctgagctata | caacctgaa | cgtggtgggc | aacgatagct | tgcgtggct | gccgcagctg | 900 |
| gaatattttt | ttctggaata | taacaacatt | cagcatctgt | ttagccatag | cctgcatggc | 960 |
| ctgtttaacg | tgcgctatct | gaacctgaaa | cgcagcttta | ccaaacagag | cattagcctg | 1020 |
| gcgagcctgc | cgaaaattga | tgattttagc | tttcagtggc | tgaaatgcct | ggaacatctg | 1080 |
| aacatggaag | ataacgatat | tccgggcatt | aaaagcaaca | tgtttaccgg | cctgattaac | 1140 |
| ctgaaatatc | tgagcctgag | caacagcttt | accagcctgc | gcaccctgac | caacgaaaacc | 1200 |
| tttgtgagcc | tggcgcatag | cccgctgcat | attctgaacc | tgaccaaaaa | caaaattagc | 1260 |
| aaaattgaaa | gcgatgcgtt | tagctggctg | ggccatctgg | aagtgctgga | tctgggcctg | 1320 |
| aacgaaattg | gccaggaact | gaccggccag | gaatggcgcg | gcctggaaaa | cattttttgaa | 1380 |
| atttatctga | gctataacaa | atatctgcag | ctgacccgca | acagctttgc | gctggtgccg | 1440 |
| agcctgcagc | gcctgatgct | gcgccgcgtg | gcgctgaaaa | acgtggatag | cagcccgagc | 1500 |
| ccgtttcagc | cgctgcgcaa | cctgaccatt | ctggatctga | gcaacaacaa | cattgcgaac | 1560 |
| attaacgatg | atatgctgga | aggcctggaa | aaactggaaa | ttctggatct | gcagcataac | 1620 |
| aacctggcgc | gcctgtggaa | acatgcgaac | ccgggcggcc | cgatttatttt | tctgaaaggc | 1680 |
| ctgagccatc | tgcatattct | gaacctggaa | agcaacggcc | ttgatgaaat | tccggtggaa | 1740 |
| gtgtttaaag | atctgtttga | actgaaaatt | attgatctgg | gcctgaacaa | cctgaacacc | 1800 |
| ctgccggcga | gcgtgtttaa | caccaggtg | agcctgaaaa | gcctgaacct | gcagaaaaac | 1860 |
| ctgattacca | gcgtggaaaa | aaaagtgttt | ggcccggcgt | ttcgcaacct | gaccgaactg | 1920 |
| gatatgcgct | taacccgtt | tgattgcacc | tgcgaaagca | ttgcgtggtt | tgtgaactgg | 1980 |
| attaacgaaa | cccataccaa | cattccggaa | ctgagcagcc | attatctgtg | caacacccg | 2040 |

```
ccgcattatc atggctttcc ggtgcgcctg tttgatacca gcagctgcaa agatagcgcg    2100
ccgtttgaac tgttttttat gattaacacc agcattctgc tgattttttat ttttattgtg    2160 ctgctgattc attttgaagg ctggcgcatt agctttttatt ggaacgtgag cgtgcatcgc    2220
gtgctgggct ttaaagaaat tgatcgccag accgaacagt tgaatatgc ggcgtatatt     2280 attcatgcgt ataaagataa agattgggtg tgggaacatt ttagcagcat ggaaaaagaa    2340
gatcagagcc tgaaattttg cctggaagaa cgcgattttg aagcgggcgt gtttgaactg    2400
gaagcgattg tgaacagcat taaacgcagc cgcaaaatta ttttttgtgat tacccatcat    2460 ctgctgaaag atccgctgtg caaacgcttt aaagtgcatc atgcggtgca gcaggcgatt    2520
gaacagaacc tggatagcat tattctggtg tttctggaag aaattccgga ttataaactg    2580
aaccatgcgc tgtgcctgcg ccgcggcatg tttaaaagcc attgcattct gaactggccg    2640
gtgcagaaag aacgcattgg cgcgtttcgc cataaactgc aggtggcgct gggcagcaaa    2700
aacagcgtgc attaa                                                      2715

<210> SEQ ID NO 2
<211> LENGTH: 904
<212> TYPE: PRT
<213> ORGANISM: Artificial Sequence
<220> FEATURE:
<223> OTHER INFORMATION: Synthetic Sequence

<400> SEQUENCE: 2

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
        50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
            115                 120                 125

His Leu Met Ser Asn Ser Ile Gln Lys Ile Lys Asn Asn Pro Phe Val
        130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240
```

```
Leu Cys Leu Glu Leu Ala Asn Thr Ser Ile Arg Asn Leu Ser Leu Ser
            245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
            275                 280                 285

Val Gly Asn Asp Ser Phe Ala Trp Leu Pro Gln Leu Glu Tyr Phe Phe
            290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
            325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
            355                 360                 365

Gly Ile Lys Ser Asn Met Phe Thr Gly Leu Ile Asn Leu Lys Tyr Leu
            370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
            405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
            435                 440                 445

Gly Gln Glu Trp Arg Gly Leu Glu Asn Ile Phe Glu Ile Tyr Leu Ser
            450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
            485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
            515                 520                 525

Leu Glu Lys Leu Glu Ile Leu Asp Leu Gln His Asn Asn Leu Ala Arg
            530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
            565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
            610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
            645                 650                 655
```

-continued

```
Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu Leu
        690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
        755                 760                 765

Trp Val Trp Glu His Phe Ser Ser Met Glu Lys Glu Asp Gln Ser Leu
        770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
            805                 810                 815

Ile Thr His His Leu Leu Lys Asp Pro Leu Cys Lys Arg Phe Lys Val
                820                 825                 830

His His Ala Val Gln Gln Ala Ile Glu Gln Asn Leu Asp Ser Ile Ile
            835                 840                 845

Leu Val Phe Leu Glu Glu Ile Pro Asp Tyr Lys Leu Asn His Ala Leu
850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
                900
```

COMPOSITIONS AND METHODS FOR REGULATING PRODUCTION OF A PRECURSOR PROTEIN

CROSS RELATED APPLICATIONS

The present application claims priority to U.S. patent application Ser. No. 17/105,967, entitled Compositions and METHODS FOR REGULATING PRODUCTION OF A PRECURSOR PROTEIN, filed Nov. 27, 2020, the disclosure of which is incorporated herein by reference.

TECHNICAL FIELD

The present disclosure generally relates to compositions and methods for regulating production of a precursor protein. In particular, the present disclosure relates to compositions and methods for regulating production of a precursor protein that can be post-translationally modified to produce a protein of the toll-like receptor family.

BACKGROUND

The mammalian immune system can differentiate between self and foreign matter. A number of cascades of signaling molecules and immune cells are characterized by their ability to recognize foreign matter and to call upon the production and stimulation of effector cells of the immune system to kill, break down, consume, or sheath the foreign matter in order to protect a host.

One mechanism by which the immune system can differentiate between self and foreign matter relates to a class of pattern recognition receptors that can detect molecular patterns that foreign microbes present. These pattern recognition receptors can be present on the phospholipid bilayer of various cell types and these cells can become activated upon a binding event between the pattern recognition receptors and the foreign molecular patterns. Activation of these cells reflects triggering of the innate immune system and the acquired immune system.

It is known that under various conditions the immune system can become dysregulated. A dysregulated immune system can cause further damage to the host, thereby preventing healing. It may also result in a loss of homeostatic controls and/or a chronically stimulated immune system.

SUMMARY

Some embodiments of the present disclosure relate to compositions and methods that upregulate the production of a precursor protein. The precursor protein may be subjected to one or more post-translational modification processes to produce a protein that is a member of the toll-like receptor (TLR) family of proteins. In some embodiments of the present disclosure, the precursor protein is a precursor of TLR3. When the precursor protein is subjected to one or more post-translational modification processes, the TLR3 protein product is bioavailable and functionally equivalent to a TLR3 protein that is produced within a subject without the benefit of the embodiments of this disclosure.

In some embodiments of the present disclosure, the compositions described herein comprise a recombinant oncolytic virus vector (ROVV) that includes an insert sequence of nucleic acids. The insert sequence encodes for the production of the precursor protein. Within the subject's cells, the insert sequence is expressed and/or replicated. Expression of the insert sequence by one or more cells of the subject results in an increased production of the precursor protein. In some embodiments of the present disclosure, the methods that upregulate the production of precursor protein relate to methods of manufacturing and administering the composition.

Some embodiments of the present disclosure relate to compositions and methods that can be used as a therapy or a treatment for a subject that has a condition whereby the subject's immune system is, or is likely to become, dysregulated.

Some embodiments of the present disclosure relate to a ROVV. The ROVV comprises a nucleotide sequence encoding a promotor and the production of the precursor protein.

Some embodiments of the present disclosure relate to an insert for use with an ROVV, wherein the insert has a nucleotide sequence according to SEQ ID 1.

Some embodiments of the present disclosure relate to a method of making an agent/target cell complex, the method comprising a step of administering a therapeutically effective amount of the agent to a subject, wherein the agent/target cell complex increases the subject's production of the precursor protein.

Some embodiments of the present disclosure relate to a pharmaceutical agent that comprises an agent, a pharmaceutically acceptable carrier and/or an excipient. Administering the pharmaceutical agent to a subject may increase the subject's production of the precursor protein.

Some embodiments of the present disclosure relate to a method of treating a condition. The method comprises a step of administering to a subject a therapeutically effective amount of an agent that upregulates the subject's production of the precursor protein.

Some embodiments of the present disclosure relate to a use of an agent for treating a condition, wherein the agent upregulates the subject's production of the precursor protein.

Embodiments of the present disclosure relate to at least one approach for inducing endogenous production of the precursor protein. A first approach utilizes one or more ROVVs containing nucleotide sequences for increasing the endogenous production of the precursor protein. The one or more ROVVs can be administered to a subject to increase the subject's production of the precursor protein.

Without being bound by any particular theory, the one or more ROVVs may be expressed in cells of the subject that already have the capability to produce, and do or may have produced, the precursor protein. These cells are referred to herein as capable cells. Therefore, the administration of the one or more vectors may increase the production of the precursor protein within those capable cells. The one or more ROVVs may also be expressed in other cells of the subject that do not produce the precursor protein when the subject is in a homeostatic state, an infection state or a disease state. These cells are not capable of producing the precursor protein without the one or more vectors of the present disclosure being expressed therein and, therefore, these cells may be referred to herein as incapable cells. The administration of the one or more vectors may induce the incapable cells to start producing the precursor protein.

The precursor protein can be subjected to one or more post-translational modification processes, which results in subject cells that are producing the precursor protein to produce a final protein-product that is bioavailable and functional. In some embodiments of the present disclosure, the protein product may be a receptor protein that is capable of participating in a binding event with a ligand. When a binding event occurs, the receptor protein may initiate one or more changes in the internal cell-signaling and metabolism of the subject cells. In some embodiments of the present disclosure, the protein product is a membrane-bound receptor protein. In the case of capable cells, the one or more ROVVs of the present disclosure may cause the capable cells to be more sensitive to ligands by increasing the number of membrane-bound receptors that can participate in binding events. In the case of incapable cells, the one or more ROVVs may cause incapable cells to become able to participating in binding events with ligands. In other words, the embodiments of the present disclosure may cause incapable cells to become responsive to a ligand that binds to the membrane-bound receptor product.

In some embodiments of the present disclosure, the membrane-bound receptor protein is a member of the toll-like receptor (TLR) family. Without being bound to any particular theory, the embodiments of the present disclosure may cause capable cells to increase their participation in the innate immune system, the acquired immune system; binding events with other TLR ligands or combinations thereof. Furthermore, incapable cells that produce the precursor protein due to the one or more ROVVs of the present disclosure, may now be able to participate in binding events with TLR ligands whereas such binding events would not otherwise occur.

Without being bound by any particular theory, TLR3 is a known component of the innate and acquired immune systems. TLR3 participates in activating immune cells upon a binding event with foreign matter due to the ability of TLR3 to recognize patterns that foreign matter present. Furthermore, pharmaceutical agents may also participate in binding events with TLR3 and these pharmaceutical TLR3 agonists may increase the efficacy of other chemotherapies for cancer, such as inhibitors of checkpoint proteins. For example, increased expression and/or functionality of TLR3 may increase the activity of polyIC, a synthetic double stranded RNA. Without being bound by any particular theory, the embodiments of the present disclosure may ultimately increase the amount of TLR3 expressed and functioning in a subject and that subject may then further benefit from treatment with other oncolytic viruses, as compared to treatment with a ROVV alone.

DETAILED DESCRIPTION

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used herein, the term "activity" is used interchangeably with the term "functionality" and both terms refer to the physiologic action of biomolecule.

As used herein, the term "agent" refers to a substance that, when administered to a subject, causes one or more chemical reactions and/or one or more physical reactions and/or or one or more physiological reactions and/or one or more immunological reactions in the subject. In some embodiments of the present disclosure, the agent is a plasmid vector.

As used herein, the term "ameliorate" refers to improve and/or to make better and/or to make more satisfactory.

As used herein, the term "biomolecule" refers to a carbohydrate, a protein, an amino acid sequence, a nucleic acid, a lipid, a primary metabolite, a secondary metabolite or another metabolite that is found within a subject. A biomolecule may be endogenous or exogenous to a subject.

As used herein, the term "cell" refers to a single cell as well as a plurality of cells or a population of the same cell type or different cell types. Administering an agent to a cell includes in vivo, in vitro and ex vivo administrations and/or combinations thereof.

As used herein, the term "complex" refers to an association, either direct or indirect, between one or more particles of an agent and one or more target cells. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, and/or any post-translational modifications of one or more proteins.

As used herein, the terms "dysregulation" and "dysregulated" refer to situations or conditions wherein homeostatic control systems have been disturbed and/or compromised so that one or more metabolic, physiologic and/or biochemical systems within a subject operate partially or entirely without said homeostatic control systems.

As used herein, the term "effector molecule" refers to a molecule within a subject that can directly or indirectly regulate the metabolic activity of a target cell by increasing or decreasing the production of DNA, RNA and/or amino-acid sequences and/or by increasing or decreasing any post-translational modifications of one or more proteins.

As used herein, the term "endogenous" refers to the production and/or modification of a molecule that originates within a cell of a subject.

As used herein, the term "excipient" refers to any substance, not itself an agent, which may be used as a component within a pharmaceutical composition or a medicament for administration of a therapeutically effective amount of the agent to a subject. Additionally, or alternatively, an excipient may, either alone or in combination with further chemical components, improve the handling and/or storage properties and/or permit or facilitate formation of a dose unit of the agent. Excipients include, but are not limited to, one or more of: a binder, a disintegrant, a diluent, a buffer, a taste enhancer, a solvent, a thickening agent, a gelling agent, a penetration enhancer, a solubilizing agent, a wetting agent, an antioxidant, a preservative, a surface active agent, a lubricant, an emollient, a substance that is added to mask or counteract a disagreeable odor, fragrance or taste, a substance added to improve appearance or texture of the composition and/or a substance that is used to form the pharmaceutical compositions or medicaments. Any such excipients can be used in any dosage forms according to the present disclosure. The foregoing classes of excipients are not meant to be exhaustive but are provided merely to be illustrative of what a person of skill in the art would know and would also recognize that additional types and combinations of excipients may be used to achieve delivery of a therapeutically effective amount of the agent to a subject through one or more routes of administration.

As used herein, the term "exogenous" refers to a molecule that is within a subject but that did not originate within the subject.

As used herein, the terms "inhibit", "inhibiting", and "inhibition" refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 90%, 100, or any amount of reduction in between the specifically recited percentages, as compared to native or control levels.

As used herein, the term "medicament" refers to a medicine and/or pharmaceutical composition that comprises the agent and that can promote recovery from a disease, disorder or symptom thereof and/or that can prevent a disease, disorder or symptom thereof and/or that can inhibit the progression of a disease, disorder, or symptom thereof.

As used herein, the term "patient" refers to a subject that is afflicted with a disease or disorder. The term "patient" includes human and veterinary subjects.

As used herein, the term "pharmaceutical composition" means any composition comprising, but not necessarily limited to, an agent to be administered a subject in need of therapy or treatment of a disease, disorder or symptom thereof. Pharmaceutical compositions may include additives such as pharmaceutically acceptable carriers, pharmaceutically accepted salts, excipients and the like. Pharmaceutical compositions may also additionally include one or more further active ingredients such as antimicrobial agents, antiinflammatory agents, anaesthetics, analgesics, and the like.

As used herein, the term "pharmaceutically acceptable carrier" refers to an essentially chemically inert and non-toxic component within a pharmaceutical composition or medicament that does not inhibit the effectiveness and/or safety of the agent. Some examples of pharmaceutically acceptable carriers and their formulations are described in Remington (1995, The Science and Practice of Pharmacy (19th ed.) ed. A. R. Gennaro, Mack Publishing Company, Easton, PA), the disclosure of which is incorporated herein by reference. Typically, an appropriate amount of a pharmaceutically acceptable carrier is used in the formulation to render said formulation isotonic. Examples of suitable pharmaceutically acceptable carriers include, but are not limited to: saline solutions, glycerol solutions, ethanol, N-(1(2,3-dioleyloxy)propyl)-N,N,N-trimethylammonium chloride (DOTMA), dioleolphosphotidylethanolamine (DOPE), and liposomes. Such pharmaceutical compositions contain a therapeutically effective amount of the agent, together with a suitable amount of one or more pharmaceutically acceptable carriers and/or excipients so as to provide a form suitable for proper administration to the subject. The formulation should suit the route of administration. For example, oral administration may require enteric coatings to protect the agent from degrading within portions of the subject's gastrointestinal tract. In another example, injectable routes of administration may be administered in a liposomal formulation to facilitate transport throughout a subject's vascular system and to facilitate delivery across cell membranes of targeted intracellular sites.

As used herein, the phrases "prevention of" and "preventing" refer to avoiding the onset or progression of a disease, disorder, or a symptom thereof.

As used herein, the terms "production", "producing" and "produce" refer to the synthesis and/or replication of DNA, the transcription of one or more sequences of RNA, the translation of one or more amino acid sequences, the post-translational modifications of an amino-acid sequence, and/or the production of one or more regulatory molecules that can influence the production and/or functionality of an effector molecule or an effector cell. For clarity. "production" is also be used herein to refer to the functionality of a regulatory molecule, unless the context reasonably indicates otherwise.

As used herein, the terms "promote", "promotion", and "promoting" refer to an increase in an activity, response, condition, disease process, or other biological parameter. This can include, but is not limited to, the initiation of the activity, response, condition, or disease process. This may also include, for example, a 10% increase in the activity, response, condition, or disease as compared to the native or control level. Thus, the increase in an activity, response, condition, disease, or other biological parameter can be 10%, 20%, 30%, 40%, 50%, 60%, 70%, 80%, 90%, 100%, or more, including any amount of increase in between the specifically recited percentages, as compared to native or control levels.

As used herein, the term "prophylactic administration" refers to the administration of any composition to a subject, in the absence of any symptom or indication of a disease or disorder, to prevent the occurrence and/or progression of the disease or disorder within the subject.

As used herein, the terms "signal molecule", "signalling molecule" and "regulatory molecule" can be used interchangeably and refer to a molecule that can directly or indirectly affect the production and/or functionality of an effector molecule or effector cell. Signal molecules can be enzymes or other types of biomolecules that can act as a direct ligand on a target cell or they may influence the levels or functionality of a downstream ligand or a receptor for a ligand.

As used herein, the term "subject" refers to any therapeutic target that receives the agent. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue and/or biological fluids.

As used herein, the term "target cell" refers to one or more cells and/or cell types that are deleteriously affected, either directly or indirectly, by a dysregulated immune system and/or a disease process. The term "target cell" also refers to cells that are not deleteriously affected but that are cells in which it is desired that the agent interacts.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent and the severity of the disease, disorder or symptom thereof. The subject's age, weight and genetic make-up may also influence the amount of the agent that will be a therapeutically effective amount.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and, (c) ameliorating the disease.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more additional active ingredients, or combinations thereof. The amount of agent within each unit is a therapeutically effective amount.

In embodiments of the present disclosure, the pharmaceutical compositions disclosed herein comprise an agent as described above in a total amount by weight of the composition of about 0.1% to about 95%. For example, the amount of the agent by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, an agent is a ROVV for introducing into a target cell for reproduction or transcription of an insert that comprises one or more nucleotide sequences that are carried within the ROVV. In some embodiments of the present disclosure, the ROVV is an herpes simplex 1 virus. In some embodiments of the present disclosure, the ROV is one or more of an adenovirus, an avian herpes virus, an avian pox virus, a chicken parvovirus, a Coxsackie virus, a duck encephalitis virus, an infectious bursal disease virus, a mammalian reovirus, a mammalian herpes virus, a mammalian pox virus, a Maraba virus, a measles virus, a murine leukemia virus, a Newcastles disease virus, a polio virus, a Seneca Valley virus, or a vesicular stomatitis virus.

In some embodiments of the present disclosure, the insert comprises one or more nucleotide sequences that encode for production of a precursor protein. The precursor protein is substantially similar, or substantially the same, as a translational product of a gene whose expression results in increased production of a protein that can participate in the innate immune system and/or the acquired immune system. In some embodiments of the present disclosure, the precursor protein is susceptible to one or more post-translational modification processes to create a protein product that acts as a membrane-bound receptor protein. The protein product can bind with extra-cellular ligands and initiate one or more intracellular signal pathways that change the metabolism of the associated cell.

In some embodiments of the present disclosure, the precursor protein is substantially similar, or substantially the same, as the translational product of the TLR3 gene. Following one or more post-translational modification processes, the precursor protein is converted into a protein product that has substantially similar, or substantially the same, function as the toll-like receptor 3 (TLR3) protein.

In some embodiments of the present disclosure, the precursor protein is a translational product of a nucleotide sequence that is substantially similar or substantially the same as SEQ ID No. 1, provided herein below.

In some embodiments of the present disclosure, the precursor protein has an amino acid sequence that is substantially similar or substantially the same as SEQ ID No. 2, provided herein below.

Without being bound by any particular theory, the precursor protein can be subjected to one or more post-translational modification processes within a subject's cell so that it is converted into a TLR3 protein product that has the same functionality and bioavailability as a TLR3 protein that a subject would produce without the embodiments of the present disclosure.

The present disclosure relates to one or more agents, therapies, treatments, and methods of use of the agents and/or therapies and/or treatments for initiating or upregulating production of the TLR3 precursor protein. Some embodiments of the present disclosure relate to methods for making a complex between at least one particle of an agent and at least one target cell of a subject for initiating or increasing production of the TLR3 precursor protein. The at least one target cell can be a capable cell or an incapable cell. For clarity, a capable cell is a cell that already has the capability to produce, and do or may have produced, the precursor protein. Therefore, the administration of the one or more ROVVs may increase the production of the precursor protein within those capable cells. The one or more ROVVs may also be expressed in an incapable cell. For clarity, an incapable cell is a cell of the subject that does not produce the precursor protein when the subject is in a homeostatic state, an infection state or a disease state. Incapable cells are not capable of producing the precursor protein without the one or more vectors of the present disclosure being expressed therein. The administration of the one or more ROVVs may induce the incapable cells to start producing the precursor protein. The embodiments of the present disclosure may cause at least a portion of a subject's capable cells and a portion of incapable cells to produce, in aggregate, a greater amount of the precursor protein which may then be subjected to one or more post-translational modification processes to produce a functional and bioavailable TLR3 protein product. As such, the embodiments of the present disclosure can be used as a therapy or a treatment for a subject that has a condition whereby the subject's immune system is, or is likely to become, dysregulated. For example, it is known that administering TLR3 agonists in animal models increases the efficacy of certain checkpoint protein inhibitors. Furthermore, it is known that the tumor cells of certain types of cancers may have dysfunctional TLR3 proteins. As such, the embodiments of the present disclosure may enhance the efficacy of therapies that include the administration of one or more checkpoint protein inhibitors, such as therapies that are directed at treating various types of cancer. Furthermore, the embodiments of the present disclosure may also increase the population of functional TLR3 protein products that are present on the surface of the subject's cells, including tumor cells. This may increase the efficacy of chemotherapy agents that acts as ligands for TLR3, such as those chemotherapy agents that may mimic or form segments of double stranded RNA.

In some embodiments of the present disclosure, the agent can be administered to the subject by an intravenous route, an intramuscular route, an intraperitoneal route, an intrathecal route, an intravesical route, a topical route, an intranasal route, a transmucosal route, a pulmonary route, and combinations thereof.

In some embodiments of the present disclosure, the agent can be administered to the subject by pipetting a dose of the agent into an in vitro cell culture, perfusing or immersing an ex vivo cell or tissue preparation with a solution that comprises the agent, mixing a biological fluid sample with a solution or substrate that comprises the agent, or combinations thereof.

Some embodiments of the present disclosure relate to an agent that can be administered to a subject with a condition that could benefit from an increased production of a TLR3 precursor protein that can be modified into a functional TLR3 protein. When a therapeutically effective amount of the agent is administered to the subject, the capable and incapable cells of the subject may increase the translational production of the TLR3 precursor protein, which then may be modified into functional and bioavailable TLR3 membrane-associated receptor protein.

In some embodiments of the present disclosure, administering a therapeutic amount of the agent to a subject upregulates the production, functionality or both of a TLR3 protein product by increasing the translational production of the precursor protein.

In some embodiments of the present disclosure, the agent is a ROVV used for gene therapy. The gene therapy is useful for increasing the subject's endogenous production of the TLR3 precursor protein. For example, the ROVV can contain one or more nucleotide sequences that that cause increased production of the precursor protein in both capable cells and incapable cells in which the ROVV is expressed.

In some embodiments of the present disclosure, the ROVV used for gene therapy is a virus that can be enveloped or not, replication effective or not, or combinations thereof.

In some embodiments of the present disclosure, the vector is a virus that is not enveloped and not replication effective. In some embodiments of the present disclosure, the ROVV is a herpes simplex 1 virus. In some embodiments of the present disclosure, the ROVV is one or more of an adenovirus, an avian herpes virus, an avian pox virus, a chicken parvovirus, a Coxsackie virus, a duck encephalitis virus, an infectious bursal disease virus, a mammalian reovirus, a mammalian herpes virus, a mammalian pox virus, a Maraba virus, a measles virus, a murine leukemia virus, a Newcastles disease virus, a polio virus, a Seneca Valley virus, or a vesicular stomatitis virus.

The embodiments of the present disclosure also relate to administering a therapeutically effective amount of the agent. In some embodiments of the present disclosure, the therapeutically effective amount of the agent that is administered to a patient is between about 10 and about $1 \times 10^{16}$ $TCID_{50}$/kg (50% tissue culture infective dose per kilogram of the patient's body weight). In some embodiments of the present disclosure, the therapeutically effective amount of the agent that is administered to the patient is about $1 \times 10^{13}$ $TCID_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1 \times 10^{16}$ TCP/kg.

Some embodiments of the present disclosure relate to a method for making a complex within a subject. The method comprises a step of administering a therapeutically effective amount of the agent to the subject. The complex comprises at least one particle of agent and one or more target cells. When the complex is formed, it affects a change in metabolism of the one or more target cells, which results in the target cells upregulating the production of the TLR3 precursor protein. Examples of a target cell include both capable cells and incapable cells, such as but not limited to: an innate immune cell, an acquired immune cell, an adrenal gland cell; a bile duct cell; a chondrocyte; a cochlear cell; a corneal cell; an endocardium cell; an endometrial cell; an endothelial cell; an epithelial cell; a fibroblast; a hair follicle cell; a hepatocyte; a lymph node cell; a mucosal cell; a myocyte; a neuron; a glomeruli cell; an optic nerve cell; an osteoblast; an ovarian tissue cell; a pancreatic islet beta cell; a pericardium cell; a platelet; a red blood cell (RBC); a retinal cell; a scleral cell; a Schwann cell; a T cell; a testicular tissue cell; a thyroid gland cell; a uveal cell; a tumor cell, or combinations thereof.

Some embodiments of the present disclosure relate to a therapy, or method of treating a condition, that can be administered to a subject with the condition. The therapy comprises a step of administering to the subject a therapeutically effective amount of an agent that will upregulate the subject's production of the TLR3 precursor protein. The increased production of the TLR3 precursor protein may result in increased levels of functional and bioavailable TLR3 protein product, which may reduce deleterious effects of the condition upon the subject.

Below are examples of a nucleotide sequence that may be present in the insert. As will be appreciated by those skilled in the art, minor modifications, substitutions or replacements of a select few nucleotides or amino acids in the sequences provided below will not substantially impact the physiologic or biologic effect of such modified sequences, as compared to the sequences provided herein below. Any such modified sequences are also contemplated by the present disclosure.

(nucleotide sequence for transcription of precursor protein)

SEQ ID No. 1

```
atgcgccaga ccctgccgtg catttatttt tggggcggcc tgctgccgtt tggcatgctg      60
tgcgcgagca gcaccaccaa atgcaccgtg agccatgaag tggcggattg cagccatctg     120
aaactgaccc aggtgccgga tgatctgccg accaacatta ccgtgctgaa cctgacccat     180
aaccagctgc gccgcctgcc ggcggcgaac tttacccgct atagccagct gaccagcctg     240
gatgtgggct ttaacaccat tagcaaactg aaccggaac tgtgccagaa actgccgatg      300
ctgaaagtgc tgaacctgca gcataacgaa ctgagccagc tgagcgataa aacctttgcg     360
ttttgcacca acctgaccga actgcatctg atgagcaaca gcattcagaa aattaaaaac     420
aacccgtttg tgaaacagaa aaacctgatt accctggatc tgagccataa cggcctgagc     480
agcaccaaac tgggcaccca ggtgcagctg gaaaacctgc aggaactgct gctgagcaac     540
aacaaaattc aggcgctgaa aagcgaagaa ctggatattt tgcgaacag cagcctgaaa      600
aaactggaac tgagcagcaa ccagattaaa gaatttagcc cgggctgctt tcatgcgatt     660
ggccgcctgt ttggcctgtt tctgaacaac gtgcagctgg cccgagcct gaccgaaaaa      720
ctgtgcctgg aactggcgaa caccagcatt cgcaacctga gcctgagcaa cagccagctg     780
agcaccacca gcaacaccac ctttctgggc ctgaaatgga ccaacctgac catgctggat     840
ctgagctata caacctgaa cgtggtgggc aacgatagct tgcgtggct gccgcagctg       900
gaatattttt tctggaata taacaacatt cagcatctgt ttagccatag cctgcatggc      960
ctgtttaacg tgcgctatct gaacctgaaa cgcagcttta ccaaacagag cattagcctg    1020
gcgagcctgc cgaaaattga tgattttagc tttcagtggc tgaaatgcct ggaacatctg    1080
aacatggaag ataacgatat tccgggcatt aaaagcaaca tgtttaccgg cctgattaac    1140
ctgaaatatc tgagcctgag caacagcttt accagcctgc gcaccctgac caacgaaacc    1200
tttgtgagcc tggcgcatag cccgctgcat attctgaacc tgaccaaaaa caaaattagc    1260
aaaattgaaa gcgatgcgtt tagctggctg ggccatctgg aagtgctgga tctgggcctg    1320
aacgaaattg gccaggaact gaccggccag gaatggcgcg cctggaaaaa cattttgaa     1380
atttatctga gctataacaa atatctgcag ctgacccgca acagctttgc gctggtgccg    1440
agcctgcagc gcctgatgct gcgccgcgtg gcgctgaaaa acgtggatag cagcccgagc    1500
ccgtttcagc cgctgcgcaa cctgaccatt ctggatctga gcaacaacaa cattgcgaac    1560
attaacgatg atatgctgga aggcctggaa aaactggaaa ttctggatct gcagcataac    1620
aacctggcgc cctgtggaa acatgcgaac ccgggcggcc cgatttattt tctgaaaggc     1680
ctgagccatc tgcatattct gaacctggaa agcaacggct tgatgaaat tccggtggaa     1740
gtgtttaaag atctgtttga actgaaaatt attgatctgg gcctgaacaa cctgaacacc    1800
ctgccggcga gcgtgtttaa caaccaggtg agcctgaaaa gcctgaacct gcagaaaaac    1860
ctgattacca gcgtggaaaa aaagtgtttt ggcccggcgt tcgcaacct gaccgaactg      1920
gatatgcgct ttaacccgtt tgattgcacc tgcgaaagca ttgcgtggtt tgtgaactgg    1980
attaacgaaa cccataccaa cattccggaa ctgagcagcc attatctgtg caacaccccg    2040
ccgcattatc atggctttcc ggtgcgcctg tttgatacca gcagctgcaa agatagcgcg    2100
ccgtttgaac tgttttttat gattaacacc agcattctgc tgattttat ttttattgtg     2160
ctgctgattc attttgaagg ctggcgcatt agcttttatt ggaacgtgag cgtgcatcgc    2220
gtgctgggct ttaaagaaat tgatcgccag accgaacagt ttgaatatgc ggcgtatatt    2280
attcatgcgt ataagataa agattgggtg tgggaacatt ttagcagcat ggaaaaagaa     2340
gatcagagcc tgaaattttg cctggaagaa cgcgattttg aagcgggcgt gtttgaactg    2400
```

```
gaagcgattg tgaacagcat taaacgcagc cgcaaaatta tttttgtgat tacccatcat    2460
ctgctgaaag atccgctgtg caaacgcttt aaagtgcatc atgcggtgca gcaggcgatt    2520
gaacagaacc tggatagcat tattctggtg tttctggaag aaattccgga ttataaactg    2580
aaccatgcgc tgtgcctgcg ccgcggcatg tttaaaagcc attgcattct gaactggccg    2640
gtgcagaaag aacgcattgg cgcgtttcgc cataaactgc aggtggcgct gggcagcaaa    2700
aacagcgtgc attaa                                                     2715
```

(amino acid sequence for TRL3 precursor protein)
SEQ ID No. 2

```
MRQTLPCIYFWGGLLPFGMLCASSTTKCTVSHEVADCSHLKLTQVPDDLPTNITVLNLTH

NQLRRLPAANFTRYSQLTSLDVGFNTISKLEPELCQKLPMLKVLNLQHNELSQLSDKTFA

FCTNLTELHLMSNSIQKIKNNPFVKQKNLITLDLSHNGLSSTKLGTQVQLENLQELLLSN

NKIQALKSEELDIFANSSLKKLELSSNQIKEFSPGCFHAIGRLFGLFLNNVQLGPSLTEK

LCLELANTSIRNLSLSNSQLSTTSNTTFLGLKWTNLTMLDLSYNNLNVVGNDSFAWLPQL

EYFFLEYNNIQHLFSHSLHGLFNVRYLNLKRSFTKQSISLASLPKIDDFSFQWLKCLEHL

NMEDNDIPGIKSNMFTGLINLKYLSLSNSFTSLRTLTNETFVSLAHSPLHILNLTKNKIS

KIESDAFSWLGHLEVLDLGLNEIGQELTGQEWRGLENIFEIYLSYNKYLQLTRNSFALVP

SLQRLMLRRVALKNVDSSPSPFQPLRNLTILDLSNNNIANINDDMLEGLEKLEILDLQHN

NLARLWKHANPGGPIYFLKGLSHLHILNLESNGFDEIPVEVFKDLFELKIIDLGLNNLNT

LPASVFNNQVSLKSLNLQKNLITSVEKKVFGPAFRNLIELDMRFNPFDCTCESIAWFVNW

INETHTNIPELSSHYLCNTPPHYHGFPVRLFDTSSCKDSAPFELFFMINTSILLIFIFIV

LLIHFEGWRISFYWNVSVHRVLGFKEIDRQIhQFEYAAYIIHAYKDKDWVWEHFSSMEKE

DQSLKFCLEERDFEAGVFELEAIVNSIKRSRKIIFVITHHLLKDPLCKRFKVHHAVQQAI

EQNLDSIILVFLEEIPDYKLNHALCLRRGMFKSHCILNWPVQKERIGAFRHKLQVALGSK

NSVH
```

Example 1—Expression Cassette

Expression cassettes for expressing a precursor protein were synthesized. Each cassette contained a CMV promotor, followed by the sequence for the precursor protein. The synthesized precursor protein expression cassettes were cloned into the ROVV using the methods described by Law el al. (A New Approach to Assessing HSV-1 Recomination during Intracellular Spread. *Viruses* 2018, 10, 220), the disclosure of which is incorporated herein by reference.

Example 2—Experimental Data

Table 1 below summarizes data obtained from Vero cells that were administered an HSV-1 TLR3 ROVV and TLR3 protein levels were compared against control Vero cells that did not receive the HSV-1 TLR3 ROVV (control). Specifically, about $2.5 \times 10^6$ Vero confluent cells were administered about $3 \times 10^8$ HSV-1 TLR3 ROVV. About 48 hours later, expression levels of human TLR3 mRNA were determined by qRT-PCR, and converted to expressed TLR3 protein levels.

TABLE 1

| | TLR3 Protein Levels | | |
|---|---|---|---|
| Molecule | Control (ag) | HSV-1 TLR3 ROVV recipient (ag) | P-value |
| TLR3 | 4 | 45 | 0.0052 | n.b. ag = attogram $1 \times 10^{-18}$ grams

As shown in Table 1, cells that received the HSV-1 TLR3 ROVV that included SEQ ID No. 1 and that encoded for increased production of a TLR3 precursor protein demonstrated statistically significant higher amounts of TLR3 than the control cells that did not receive the HSV-1 TLR3 ROVV. Without being bound by any particular theory, the cells that were administered the HSV-1 TLR3 ROVV had higher levels of TLR3 than cells that did not receive the HSV-1 TLR3 ROVV.

The invention claimed is:

1. A recombinant oncolytic virus vector (ROVV), the ROVV comprising an oncolytic virus containing:
   a) a promotor, followed by:
   b) a nucleotide sequence encoding a toll-like receptor 3 (TLR3) precursor protein, wherein the nucleotide sequence is SEQ ID No. 1.

2. The ROVV of claim 1, wherein the ROVV is a herpes simplex 1 virus.

3. The ROVV of claim 1, wherein the ROVV is one of an adenovirus, an avian herpes virus, an avian pox virus, a chicken parvovirus, a Coxsackie virus, a duck encephalitis virus, an infectious bursal disease virus, a mammalian reovirus, a mammalian herpes virus, a mammalian pox virus, a Maraba virus, a measles virus, a murine leukemia virus, a Newcastles disease virus, a polio virus, a Seneca Valley virus, or a vesicular stomatitis virus.

* * * * *